United States Patent
Tröhler et al.

(10) Patent No.: US 10,460,393 B2
(45) Date of Patent: Oct. 29, 2019

(54) CONVERTIBLY TRIGGERED INSURANCE SYSTEM WITH A LAYERED TRIGGER STRUCTURE AND CORRESPONDING METHOD THEREOF

(71) Applicant: SWISS REINSURANCE COMPANY LTD., Zurich (CH)

(72) Inventors: Claudio Tröhler, Zurich (CH); Andreas Schäfli, New York, NY (US); Alexander Bosch, Exeter (GB); Sherman Power, Naperville, IL (US); Patrick Roder, Baar (CH); Andrea Scascighini, Brookfield, CT (US)

(73) Assignee: SWISS REINSURANCE COMPANY LTD., Zurich (CH)

( * ) Notice: Subject to any disclaimer, the term of this patent is extended or adjusted under 35 U.S.C. 154(b) by 624 days.

(21) Appl. No.: 15/203,887

(22) Filed: Jul. 7, 2016

(65) Prior Publication Data
US 2017/0004581 A1    Jan. 5, 2017

Related U.S. Application Data

(63) Continuation of application No. PCT/EP2015/064904, filed on Jun. 30, 2015.

(51) Int. Cl.
| | |
|---|---|
| *G06Q 40/00* | (2012.01) |
| *G06Q 40/08* | (2012.01) |
| *G06Q 10/10* | (2012.01) |
| *G06Q 10/06* | (2012.01) |
| G06Q 40/02 | (2012.01) |
| G06Q 50/10 | (2012.01) |
| G06Q 50/22 | (2018.01) |

(52) U.S. Cl.
CPC ........ *G06Q 40/08* (2013.01); *G06Q 10/0635* (2013.01); *G06Q 10/10* (2013.01); *G06Q 10/063* (2013.01); *G06Q 40/02* (2013.01); *G06Q 50/10* (2013.01); *G06Q 50/22* (2013.01)

(58) Field of Classification Search
CPC ........................................................ G06Q 40/08
USPC .......................................................... 705/3, 4
See application file for complete search history.

(56) References Cited

U.S. PATENT DOCUMENTS

2014/0324466 A1 * 10/2014 Wertzberger ......... G06F 19/328
                                                                       705/3

OTHER PUBLICATIONS

International Search Report and Written Opinion dated Feb. 23, 2016 in PCT/EP2015/064904 filed Jun. 30, 2015.

* cited by examiner

*Primary Examiner* — Samica L Norman
(74) *Attorney, Agent, or Firm* — Oblon, McClelland, Maier & Neustadt, L.L.P.

(57) ABSTRACT

A system for providing a dynamically morphing, self-sufficient risk protection structure, the system including: risk exposure components that are connected to a first insurance system of the system and that transfer risk exposure associated with an occurrence of defined risk events from the risk exposure components to the first insurance system based on equitable, mutually aligned first risk transfer parameters and correlated aligned first payment transfer parameters, and the first insurance system that is connected to a second insurance system of the system and that transfers risk exposure associated with the occurrence of the defined risk events from the first insurance system to the second insurance system based on equitable, mutually aligned second risk transfer parameters and correlated aligned second payment transfer parameters.

18 Claims, 3 Drawing Sheets

CONVERTIBLY TRIGGERED INSURANCE SYSTEM WITH A LAYERED TRIGGER STRUCTURE AND CORRESPONDING METHOD THEREOF

CROSS REFERENCE TO RELATED APPLICATION

This application is a Continuation of PCT International Application No. PCT/EP2015/064904, filed on Jun. 30, 2015, the entire contents of which are incorporated herein by reference.

FIELD OF THE INVENTION

The present invention relates to triggered insurance systems, in particular triggered insurance systems with a layered morphing risk transfer structure providing risk protection for defined risk exposure components, in particular coupling systems for automated insurance systems, that offer risk sharing for risk exposure components by providing dynamic self-sufficient risk protection for the risk exposure components by means of two complementary coupled insurance systems; e.g., an insurance system and a reinsurance system. More particularly, the invention relates to an event-driven switched trigger structure for the complementary switching of two coupled, autonomously operated resource pooling systems in order to provide risk protection with regard to the pooled risk exposure components by means of the two complementary or supplementary activated resource pooling systems associated with the system.

BACKGROUND OF THE INVENTION

Risk transfer techniques are vastly employed and implemented in many prior art risk management systems and insurance technology systems. Thus, in the last decade, apart from the traditional channels of financing risks, alternative routes based on automated, self-sufficient risk transfer systems and/or insurance systems have been developed. Self-sufficiency or self-containment in the context of this document means directed to system with automated operation. Thus, self-sufficiency defines an operation state of not requiring any aid, support, or interaction, for keeping up the operation, i.e. the system able to provide a survival of its operation independent of any human interaction. Therefore, it is a type of operational autonomy of an automated system. On an operational automation scale, a system with totally self-sufficient operation does not need external adjustment for its operation to initiate or uphold its operation, i.e. is able to work in operational autarky. The present invention extends this technology to a layered risk transfer technique with a mutually tuned trigger structure, thereby reinforcing the importance of developing automated systems allowing a self-sufficient operation. Mutually tuned means, that the trigger parameter of the trigger structure are mutually adapted and negotiated between the trigger layers. It is a necessary pre-requirement for the technical operation of such systems that the involved payment and cash flow management devices be employed to match different segments of loss distribution, as e.g. stop loss and reverse development cover distributions. The layered structure of the system of the present invention allows for a new form of restructuring the underlying risk management resources or capital combining prospective and adverse or retrospective effects by capturing appropriate parameters.

Loss prevention systems and optimized insurance systems have long been and still are the most important part in automatized risk transfer systems to provide effective protection against various types of risks. Modern insurance systems have been largely concentrated on the problem of how a large number of risk-averse components can beneficially and automatically transfer their risks. Since the underlying problem has a statistical nature, the likelihood of a risk transfer system being triggered by a risk event comes close to certainty over an appropriate long time horizon, and the operation of the system thus cannot be steered by the condition of measuring the occurrence of a risk event, but rather when such a risk event is measured. An optimized operation of a risk transfer or insurance system depends on its structure and tuning based on the ability to predict future risk event measurements. The level of uncertainty is high, since it affects the risk transfer structure and operation of the system. To relieve this problem, one of the characteristics of risk transfer systems is the pooling of risks and risk transfers. In the prior art, the pooling of risk transfers can typically involve the grouping, selecting and filtering of various risk exposures, so that the law of large numbers can operate to provide a more accurate prediction of future losses. From a technical point of view, if the losses associated with risk transfer are more predicable, the operation and management of the actual risk transfers can be optimized. Additional risk transfer is another important element, where first risk transfer or insurance systems can optimize or stabilize operation by partially shifting pooled risks to a third system, as a second insurance system.

Automated systems for risk transfer have been used for quite some time in the state of the art as a technical tool to manage the risk of uncertain losses, in particular to keep up operation of functional, technical or business units. These days, significant risk exposure is associated with many aspects in the life and non-life sectors. Risk exposed units, such as any kinds of objects, individuals, corporate bodies and/or legal entities, are necessarily confronted with many forms of active and passive risk management to hedge and protect against the risk of certain losses and events. The prior art addresses such risks of loss, for example, based on transferring and pooling the risk of loss from a plurality of risk exposed entities to a dedicated pooling entity. In essence, this can be executed by effectively allocating the risk of loss to this pooling unit or entity in that the resources of associated units, which are exposed to a certain risk, are pooled. If one of the units is hit by an event that is linked to a transferred risk, the pooling entity directly intercepts the loss or damage caused by the event by transferring resources from the pooled resources to the affected unit. Pooling of resources can be achieved by exchanging predefined amounts of resources with the resource-pooling system; e.g., payments or premiums that are to be paid for the transfer of the risk. This means that predefined resource amounts are exchanged for the other unit, thereby assuming the risk of loss.

As described above, insurance systems use resource pooling systems to pool the resources and risks of associated risk-exposed components. However, to avoid operational instabilities, often such resource pooling systems of an insurance system are coupled to one or more other resource pooling systems in order to redistribute parts of their pooled risks. Correspondingly, a loss that is to be covered can be segmented by those coupled insurance systems, wherein in order to switch from one insurance system to another insurance system, technically a risk transfer structure must be provided by the systems.

Typically, risk associated with risk-exposed components can roughly be divided in three categories, i.e., expected risks, unexpected risks and catastrophic risks. The systems covering expected risks can simply be based on setting an appropriate threshold value for a resource retention, which should equalize the amount of pooled risks. The unexpected risks, e.g., operational risks, risk based on an excessively low selected retention level, or risks occurring out of IBNR losses, i.e., incurred but not [yet] reported, cover prospective as well as retrospective risk covers, or so-called adverse development cover (ADC). The last part of possible losses concerning catastrophic risks are technically even more difficult to capture, since they do not obey the law of large numbers. Traditional prior art systems are directed to catastrophic derivatives, securitization and contingency financing, in particular to transfer risks by appropriate structures to the capital market. Due to the different characteristics of the risks to be captured, the prior art systems fail to cover different risk transfers from different categories, in particular since the operation of prior art systems needs to be specifically adapted and optimized to cope with specific risk characteristics. Thus, in the prior art, each specific type of risk event needs to be covered by a different risk transfer system or mechanisms, which makes the operation and optimization of the risk cover difficult and confusing for risk-exposed components. The goal of minimizing the total risk exposure of a risk-exposed component and/or an insurance system under different boundary criteria, such as criteria of value at risk or conditional value at risk, i.e., by finding the optimal balance between the benefit (reducing the risk by purchasing reinsurance shares) and the cost (premiums) of the redistributed insurance risk shares, is difficult to achieve. Therefore, the object of the present invention addresses the technical problem of coupling two automated resource pooling systems with the goal of pooling the risk exposure of associated components and seeking better and more effective technical implementations based on an appropriate risk transfer structure covering the different aforementioned risk categories, i.e. is broader in its applicable scope and easier to be placed.

The prior art specifies a plurality of systems addressing the above-mentioned problem. For example, US 2004/0236698 A1 describes a system for automated risk management trade between two coupled systems; in particular, an insurance system and a reinsurance system. This system provides for the transfer of premiums and loss payments directly between the risk-pooling systems. Further, the system allows for interactions between the two coupled systems, which allows for decision-making functions concerning reinsurance products. However, US 2004/0236698 A1 does not describe how a transfer structure should be designed for a specific system, or how the insurance system should optimize its own risk exposure for the process of determining the mitigation of its own risk. Another example of the known prior art in the field of automated risk transfer systems is US 2011/0112870 A1. US 2011/0112870 A1 discloses a system for determining a percentage for assigning, i.e., transfer-related risk in an insurance pool, wherein the transferred risks are shared via a secondary resource pooling system that is based on predefined transfer-specific conditions of a reinsurance contract. The system mainly allows for automatically providing information regarding losses, which is transferred to the captive resource pooling system in the insurer's system and the reinsurer's system. However, US 2011/0112870 A1 does not disclose a general method for determining the amount of the actual risk transfer or covering different risk categories. Still another example of a prior art patent in the field of optimal risk transfer strategies is U.S. Pat. No. 7,970,682 B1. U.S. Pat. No. 7,970,682 B1 discloses a system that automatically provides a primary resource pooling system's risk transfer structure to accommodate the long-standing exposure of liabilities, achieve significant risk transfer to a third party (reinsurer), reduce potential financial reporting inconsistencies between hedge assets and liabilities, decrease operational risk, and lastly, reduce exposure to rollover risk (due to changes in the cost of hedging instruments); i.e., in effect, tools for ensuring the operational stability of the primary resource pooling system. U.S. Pat. No. 7,970,682 B1 is not specifically directed at the risk transfer structures of the pooled risk of a primary resource and risk pooling system; instead, U.S. Pat. No. 7,970,682 B1 is another example for an adaption of a primary insurance system's risk strategies. However, nothing in the prior art provides a system for a risk transfer structure capable of covering different categories of risks.

In summary, in the prior art, existing systems, whose operations are at least partially based on risk transfer schemes or structures, come in many different forms, often with very different objectives and operational approaches. However, typically, the range of schemes or structures of the prior art systems are specific to one particular risk, risk category, locality, sector or country, supporting the view that there is no 'one-size-fits-all' solution in the prior art.

SUMMARY OF THE INVENTION

It is one object of the present invention to provide a system and method for sharing the risk of risk events of a variable number of risk exposure components by providing dynamic, self-sufficient risk protection for the risk exposure components covering different risk categories, i.e., expected, unexpected and catastrophic risks; this is achieved by means of the present invention extending the technology to a layered risk transfer technique with a mutually tuned trigger structure, thereby reinforcing the importance of developing automated systems allowing self-sufficient operation. In particular, the present invention is realized by means of a primary resource-pooling system, which is stabilized and optimized by a triggered, stop loss risk transfer structure to at least one secondary resource-pooling system and further morphing the stop loss risk transfer structure, after a threshold time period, into a risk transfer structure triggering adverse development parameters. I.e. the system morphs after the event is measured and triggered (e.g. at the end of a defined period (threshold time period, contracted period) provided that the trigger event occurred. As an embodiment variant, the system commutes the adverse development cover (ADC), i.e. the adverse development risk transfer, after a period of e.g. 5-10 years. This has the advantage of limiting the tail exposure but allowing enough time for the reserves to reach a more or less stable level in respect to the operation of the system. Further, it expedites the cash flows for the primary risk transfer system, i.e. the first, automated, coupled insurance system, and reduces the administrative burden of all involved parties caused by extremely long payout patterns (i.e. small partial payments over a period of time of e.g. 40 years). In particular, the system provides an automated switching mechanism between the two coupled systems as well as between the two kinds of risk transfer structures and offers a measure for the optimization of the systems. Another object of the invention seeks to provide a way to technically capture, handle and automate complex, related risk transfer structures and switching operations of the insurance industry that are related to optimally shared risks and transfer operations. Another object of the invention seeks to synchronize and adjust such operations based on the technical multilayered trigger structure approach. In contrast to standard practice, the resource pooling systems create a reproducible operation with the desired, technically based, repetitious accuracy that relies on technical means, process flow and process control/operation.

According to the present invention, these objects are achieved, particularly, with the features of the independent claims. In addition, further advantageous embodiments can be derived from the dependent claims and the related descriptions.

According to the present invention, the above-mentioned objects for a convertibly triggered insurance system providing self-sufficient risk protection for a variable number of defined risk exposure components are achieved, particularly, in that the risk exposure components are connected to a first or primary insurance system of the convertibly triggered system by transferring risk exposure associated with the occurrence of defined risk events from the risk exposure components to the first insurance system by means of equitable, mutually aligned first risk transfer parameters and correlated aligned first payment transfer parameters; in that the first insurance system is connected to a second insurance system of the convertibly triggered system by transferring risk exposure associated with the occurrence of the defined risk events from the first insurance system to the second insurance system by means of equitable, mutually aligned second risk transfer parameters and correlated aligned second payment transfer parameters; in that, if one of the defined risk events occurs, loss parameters measuring the loss at the risk exposure components are captured and transmitted to the first insurance system and wherein the occurred loss is automatically covered by the first insurance system based on the equitable, mutually aligned risk exposure parameters; in that the convertibly triggered system comprises a first layer trigger structure comprising an aggregation module for capturing and automatically aggregating captured loss parameters over all risk exposure components and all occurrences of risk events within a predefined time period by incrementing an associated stored aggregated loss parameter, i.e. for providing the appropriate stop loss functionality, wherein by triggering the aggregated loss parameter exceeding a defined stop threshold value by means of a first trigger module of the first layer trigger structure, the occurred loss exceeding the defined stop threshold value is automatically covered by the second insurance system based on the equitable, mutually aligned second risk transfer parameters; in that the convertibly triggered system comprises an intermediate layer trigger structure with an associated switching device, wherein by triggering the aggregated loss parameter exceeding said defined stop threshold value by means of the first trigger module, a second layer trigger structure of the convertibly triggered system is automatically activated via the switching device of the intermediate layer trigger structure; and in that the second layer trigger structure comprises a second trigger module, wherein if the second layer trigger structure is activated by means of the switching device by triggering loss parameters measuring the loss at the risk exposure components not to be transmitted to the convertibly triggered system within the predefined time period and to fall outside a retention threshold value of the first insurance system, the occurred loss exceeding said retention threshold value is automatically covered by the second insurance system based on the equitable, mutually aligned risk transfer parameters. One of the advantages of the convertibly triggered system is that the operational parameters of the system can be tuned by providing various retrospectively and/or prospectively layered risk transfer structures for covering and transferring first insurance systems' risk exposure with regard to or regardless of the intensity of the actually-occurring risk events. The mutual tuning of the operational parameters of the convertibly triggered system layers allows for tuning the operational parameters of various retrospective operation layers of the convertible system, such as stop loss risk transfer or excess of loss risk transfer or finite risk transfer or such as adverse development cover (ADC) of risk transfers or loss portfolio transfer (LPT) cover of risk transfers and/or together with the operational parameters of prospective or retrospective operation layers of the convertible system, such as quota share risk transfer, founded cover risk transfer, spread loss risk transfer, or in general blended cover risk transfer. In particular, for the operation of an automated risk transfer system, it is important that the system can be operated self-sufficiently, i.e., with economic finality concerning the automatically pooled and managed resources. Therefore, the convertibly triggered system makes it possible to combine stop loss cover structures with risk transfer of adverse development cover and/or loss portfolio transfer cover, providing a self-sufficient operatable, automatable risk transfer system, which cannot be found in the prior art systems. In particular, the prior art systems do not allow for mutually tuning the operational parameters of risk transfers of techniques such as stop loss transfers with techniques such as adverse development cover and/or loss portfolio transfer cover, providing an overall optimization of the parameters together with the technical requirement of self-sufficiency of the system. Another advantage is that the system provides the technical requirements for a multi-period optimization of the operational parameters of a layered risk-transfer system. Thus, as a result of the pre-defined time period, e.g., a financial year, the applied stop loss risk transfer can determine the second insurance system's limit available during run off in the form of an in-the-money adverse development cover. The invention provides supremely optimized layer-based coupling also optimizing the classically prevalent optimization problem of managing the two coupled risk transfer systems, seeking better and more effective operation and strategies based on an appropriate risk transfer structure. The system furthermore has the advantage that smaller pooled resources, in contrast to traditional coupled resource pooling systems, are sufficient to allow for a safe operation of the system. In addition, the operational aspects of the system are transparent to operators as well as covered risk units, since payment is transferred in response to individually adaptable risk transfer structures and related to certain definable triggers in the context of the information pathways. Finally, the inventive system provides a new modality for optimizing the underlying risk transfer structure in the service of risk transfer and sharing of two coupled insurance systems by using several layers of different risk transfer strategies. The invention has, inter alia, the additional strategic and operational advantage that the risk-exposed components as well as the first insurance system operationally allow for an all-inclusive balance sheet and capital protection (with some exclusions). The present convertible invention is additionally capable, due to its technical structure, of protecting against unknown accumulation, including contribution from prior years. This is not possible using the known prior art systems, since their structure is typically solely directed at single risks. The operation of the present invention also compares favourably to an Adverse Development Cover in terms of budget in view of contingent nature. The invention allows for an operational optimization, which makes it very efficient under available economic capital models underlying prior art systems, in particular also under available stochastic economic capital models. Furthermore, the present system optionally allows automatic renewal of the operation, optionally and non-optionally, and optimization of the appropriate operational parameters for an optimized coverage within the subsequent defined time period, e.g., annually. Lastly, the system of the present invention provides the technical structure to be applicable and/or operatable fall forms of accumulation risks, i.e., inter alia, classic clash risk transfers, serial aggregation risk transfers, business disaster risk transfers, systemic failure risk transfers, etc. It has to be mentioned that the conventional financial year stop loss risk transfer can be favorable from the risk exposure components perspective. However, from the operational perspective of an automated and coupled second risk transfer system, this has a couple of severe drawbacks, which drive the amount of pooled resources, i.e. the necessary premiums to be transferred, at the second coupled risk transfer system, e.g. a coupled, automated reinsurance system, to a level that is in most cases not anymore economically realizable for first or primary insurance systems. The main problem from a second coupled risk transfer system's perspective lies in the fact that the primary risk transfer system has an information advantage in regards of the expectation of the reserves development and that the primary risk transfer system can influence or even manipulate the reserve level in a way that would trigger a financial year stop loss treaty. Let's assume that the primary risk transfer system overstated the reserves by 10 in the financial year 2014 in a way that the stop loss treaty 2014 would be triggered and give a cover of 10. If in 2015 the primary risk transfer system releases the 10 in reserves again, the second risk transfer system would still need to pay under the financial year stop loss of 2014. With the Morph structure, this cheating element is addressed for the coupled systems and reduced to an extent that a financial year stop loss can be offered at an affordable price.

In one alternative embodiment, by triggering the aggregated loss parameter exceeding said defined stop threshold value and by activating the second layer trigger structure of the convertibly triggered system by means of the switching device, the first layer trigger structure is automatically set to a same time period subsequent to the predefined time period, wherein the operation of the first layer trigger structure is automatically extended to said subsequent time period and wherein the value of the incremented associated aggregated loss parameter is reset to 0. In said subsequent time period, the operation of the convertibly triggered system can for example be set to the same defined stop threshold value and same retention threshold value as defined in the preceding defined time period. This alternative embodiment has, inter alia, the advantage that it allows the convertibly triggered system to be reset automatically by automated renewal of the risk transfer and corresponding loss cover. After switching via the associated switching device, i.e., by triggering a morphing cover, it can advantageously extend the operation of the convertibly triggered system for another defined time period, i.e., to renew the cover for the subsequent time period.

The renewed covers functionality, i.e., the operational parameters of the convertibly triggered system, can remain unchanged in this embodiment. However, the convertibly triggered system can treat the previously triggered activation as inuring second insurance system risk transfer and associated loss cover. Thus, the renewed risk transfer and cover can provide the risk-exposed components with an automatically equivalent degree of risk cover over the next time period, for example if the time period is chosen as one year, on a calendar basis trigger as in the previous year. For example, an initially high attaching defined time period triggers (e.g. Financial Year (FY) triggered) aggregate stop loss risk transfer layer, providing it is not impaired, the convertible system renews it annually as a long term operation, i.e. as a 1 year cover w/o automatic renewal. The risk transfer limit from the first to the second insurance system can for example depend on the pooled resources of the previous time period, e.g., of the financial year's results, wherein the trigger refers to the same time period as the automated risk cover. The layered risk transfer structure provides protection against accumulation risk, which is of a strategic nature for the self-sufficient automated operation of the system. If the time period, e.g., the FY, aggregate stop loss is triggered, then the contract for example morphs into an in-the-money Adverse Development Cover, i.e., the aggregated stop loss threshold is triggered via the first trigger module (601), the switching device of the intermediate layer trigger structure activates the second layer trigger structure with the associated adverse development risk transfer cover. The exit point of cover can be the total exit reserves (at the end of the cover period, i.e., defined time period) and the limit provided is equal to the amount "burned" in the defined time period, e.g., the financial year, aggregate stop loss. In the alternative embodiment of the in-the-money structure, the in-the-money coverage risk transfer ensures that the full value is paid if the booked reserves, i.e., the pooled resources, are correct. Thus, the system can also comprise a paid-as-paid structure, i.e. that the risk transfer only incurs an obligation to cover by constituting a condition precedent that excuses the system from having a cover or payment obligation if the first insurance system does not transfer the payment for the risk-transfer to the second insurance system.

In one alternative embodiment, the risk exposure components can for example be connected to the first insurance system of the convertibly triggered system by means of payment-transfer modules configured for receiving and storing first payment parameters from the risk exposure components for the transfer of risks associated with the risk exposure components from the risk exposure components to the first insurance system. By analogy, the first insurance system can be connected to the second insurance system of the convertibly triggered system by means of a payment-transfer module configured for receiving and storing second payment parameters from the first insurance system for the transfer of risks associated with pooled risk exposures of the risk exposure components from the first insurance system to the second insurance system. This alternative embodiment has, inter alia, the advantage that the flow of data and payment parameters between the single system components can be completely automated, centralized, monitored and operated by the convertibly triggered system, allowing for complete technical control of the interaction of the different system components of the convertibly triggered system.

In another alternative embodiment, the switching device comprises capturing means for capturing a transfer of payment from the first insurance system to the second payment-transfer module, wherein the second layer trigger structure of the system is activatable by triggering a payment transfer matching a predefined activation threshold parameter. As a more particular alternative embodiment, a periodic payment transfer from the risk exposure components to the resource pooling system via a plurality of payment receiving modules is requested by means of a monitoring module of the resource-pooling system, wherein the risk transfer or protection for the risk exposure components is interrupted by the monitoring module, when the periodic transfer is no longer detectable via the monitoring module. As an alternative, the periodic payment transfer request can be interrupted automatically or waived by the monitoring module, when the occurrence of indicators for a risk event is triggered in the data flow pathway of a risk exposure component. These alternative embodiments have, inter alia, the advantage that the system allows for further automation of the monitoring operation, especially of its operation with regard to the pooled resources.

In another alternative embodiment, an independent verification risk event trigger of the first and/or second resource pooling system is activated in cases when the occurrence of indicators for a risk event is triggered in the data flow pathway of a risk exposure component by means of the risk event triggers, and wherein the independent verification risk event trigger additionally issues a trigger in the event of the occurrence of indicators regarding risk events in an alternative data flow pathway with independent measuring parameters from the primary data flow pathway in order to verify the occurrence of the risk event at the risk exposure component. In this alternative, the transfer of payments is only assigned to the corresponding risk exposure component if the occurrence of the risk event at the risk exposure component is verified by the independent verification risk event trigger. These alternative embodimentshave, inter alia, the advantage that the operational and financial stability of the system can thus be improved. In addition, the system is rendered less vulnerable to fraud and counterfeit.

In general, the switching device can for example comprise capturing means that capture a payment transfer assigned to one of the risk transfer layers, e.g., the stop loss risk transfer layer or the adverse development cover risk transfer, from the first insurance system to the second payment transfer module, wherein the assigned risk transfer layer is activated, and wherein the risk exposure of the first insurance system associated with the assigned risk transfer layer is transferred to the second insurance system. This alternative embodiment has, inter alia, the advantage that additionally, single risk layers of all forms of accumulated risks, such as classic clash, serial aggregation, business disasters and/or systemic failures, etc., can be activated, allowing a distinct and discrete risk transfer and risk cover from the first to the second resource pooling system.

In another alternative embodiment, the risk transfer functionality is comprised of the plurality of stored, variable risk transfer layers or structures, wherein the first resource pooling system comprises an interface module for accessing and adapting the assigned operational parameters of a layer of each of the risk transfer layers prior to the transfer of the payment sum from the first resource pooling system to the second resource pooling system. This alternative embodiment has, inter alia, the advantage that the risk transfer structure can be dynamically adjusted and, moreover, selected and/or additionally optimized directly by the first resource pooling system or the associated insurance system.

In still another alternative embodiment, the assembly module of the switching device comprises means for processing risk-related component data and for providing data regarding the likelihood of said risk exposure for one or a plurality of the pooled risk exposure components, in particular, based on risk-related component data, and wherein the receipt and preconditioned storage of payments from risk exposure components for the pooling of their risks can be dynamically determined based on the total risk and/or the likelihood of risk exposure of the pooled risk exposure components. This alternative embodiment has, inter alia, the advantage that the operation of the first and/or second resource pooling system can be dynamically adjusted to changing conditions in relation to the pooled risk, such as a change of the environmental conditions or risk distribution, or the like, of the pooled risk components. A further advantage is that the system does not require any manual adjustments, when it is operated in different environments, places or countries, because the size of the payments of the risk exposure components is directly related to the total pooled risk.

In one alternative embodiment, the assembly module of the switching device comprises means for processing risk-related component data and for providing information regarding the likelihood of said risk exposure for one or a plurality of the pooled risk exposure components, in particular, based on risk-related component data, and wherein the receipt and preconditioned storage of payments from the first resource pooling system to the second resource pooling system for the transfer of its risk can be dynamically determined based on the total risk and/or the likelihood of risk exposure of the pooled risk exposure components. This alternative embodiment has, inter alia, the advantage that the operation of the first and/or second resource pooling system can be dynamically adjusted to changing conditions of the pooled risk, such as changes of the environmental conditions or risk distribution, or the like, of the pooled risk components. A further advantage is the fact that the system does not require any manual adjustments, when it is operated in different environments, places or countries, because the size of the payments of the risk exposure components is directly related to the total pooled risk.

In one alternative embodiment, the number of pooled risk exposure components is dynamically adjusted via the first resource pooling system to a range where non-covariant, occurring risks covered by the resource pooling system affect only a relatively small proportion of the total pooled risk exposure components at any given time. Analogously, the second resource pooling system can for example dynamically adjust the number of pooled risk shares transferred from first resource pooling systems to a range where non-covariant, occurring risks covered by the second resource-pooling system affect only a relatively small proportion of the total pooled risk transfers from first resource pooling systems at any given time. This variant has, inter alia, the advantage that the operational and financial stability of the system can be improved.

In one alternative embodiment, the risk event triggers are dynamically adjusted by means of an operating module based on time-correlated incidence data for one or a plurality of risk events. This alternative embodiment has, inter alia, the advantage that improvements in capturing risk events or avoiding the occurrence of such events, for example by improved forecasting systems, etc., can be dynamically captured by the system and dynamically affect the overall operation of the system based on the total risk of the pooled risk exposure components.

In another alternative embodiment, upon each triggering of an occurrence, where parameters indicating a risk event are measured, by means of at least one risk event trigger, a total parametric payment is allocated with the triggering, and wherein the total allocated payment is transferrable upon a triggering of the occurrence. The predefined total payments can for example be leveled to any appropriate lump sum, such as a predefined value, or any other sum related to the total transferred risk and the amount of the periodic payments of the risk exposure component. This alternative has, inter alia, the advantage that the parametric payments or the payments of predefined amounts, which, as in the embodied alternative, may also depend on a first, second, third or a plurality of trigger levels, i.e., the different stages of triggers. Further, the parametric payment may allow for an adjusted payment of the total sum that can for example be dependent on the stage of the occurrence of a risk event, as triggered by the system.

In one alternative embodiment, the convertible system is provided for adaptive operation of an autonomously operated risk transfer system by providing self-sufficient risk protection of a variable number of risk exposure components by means of an automated resource-pooling system capable of pooling resources and absorbing transferred risks, wherein the risk exposure components are connected to the resource pooling system by means of a payment transfer module configured for receiving and storing payments from the risk exposure components for the pooling of their risks. The risk transfer systems can comprise or be associated with insurance systems, such as automated primary insurance systems, or any kind of financial systems or business units capable of absorbing transferred risks. For example, the inventive risk transfer system can be applied or extended to asset-based systems, such as operational units of financial institutions, etc. In this alternative embodiment, the switching device comprises a capturing device for capturing payment transfer parameters from the risk exposure components to the payment transfer module, and wherein, upon triggering a transfer of the total payment sum to the payment transfer module, the risk exposure of the risk exposure component assigned to the transfer of the payment sum is transferred to the first insurance system. In general, the convertible system or the core engine can for example comprise event-driven triggers for triggering, in a data flow pathway, measuring devices associated with the risk exposure components for the occurrence of a risk event, and wherein, if an occurrence of a risk event is triggered in the data flow pathway, the corresponding risk transfer layer and structure is determined by means of the core engine based on the measured actual loss. If a risk event occurs, an activation signal is generated by means of the switching device based on the determined risk transfer structure, e.g., the first or second layer trigger structure, and the measured actual loss, wherein the switching device triggers the activation of the resource pooling system by means of the generated activation signal by transferring the activation to the resource pooling system to provide risk protection to the risk exposure components, and wherein the activation of the resource pooling system is based on an appropriately defined risk transfer function by means of the operational parameters of the convertible system.

In addition to the system, as described above, and the corresponding method, the present invention also relates to a computer program product that includes computer program code means for controlling one or more processors of the control system such that the control system performs the proposed method; and it relates, in particular, to a computer program product that includes a computer-readable medium that contains the computer program code means for the processors.

BRIEF DESCRIPTION OF THE DRAWINGS

The present invention will be explained in more detail, by way of example, with reference to the drawings in which.

DETAILED DESCRIPTION OF THE PREFERRED EMBODIMENTS

Figure 1:
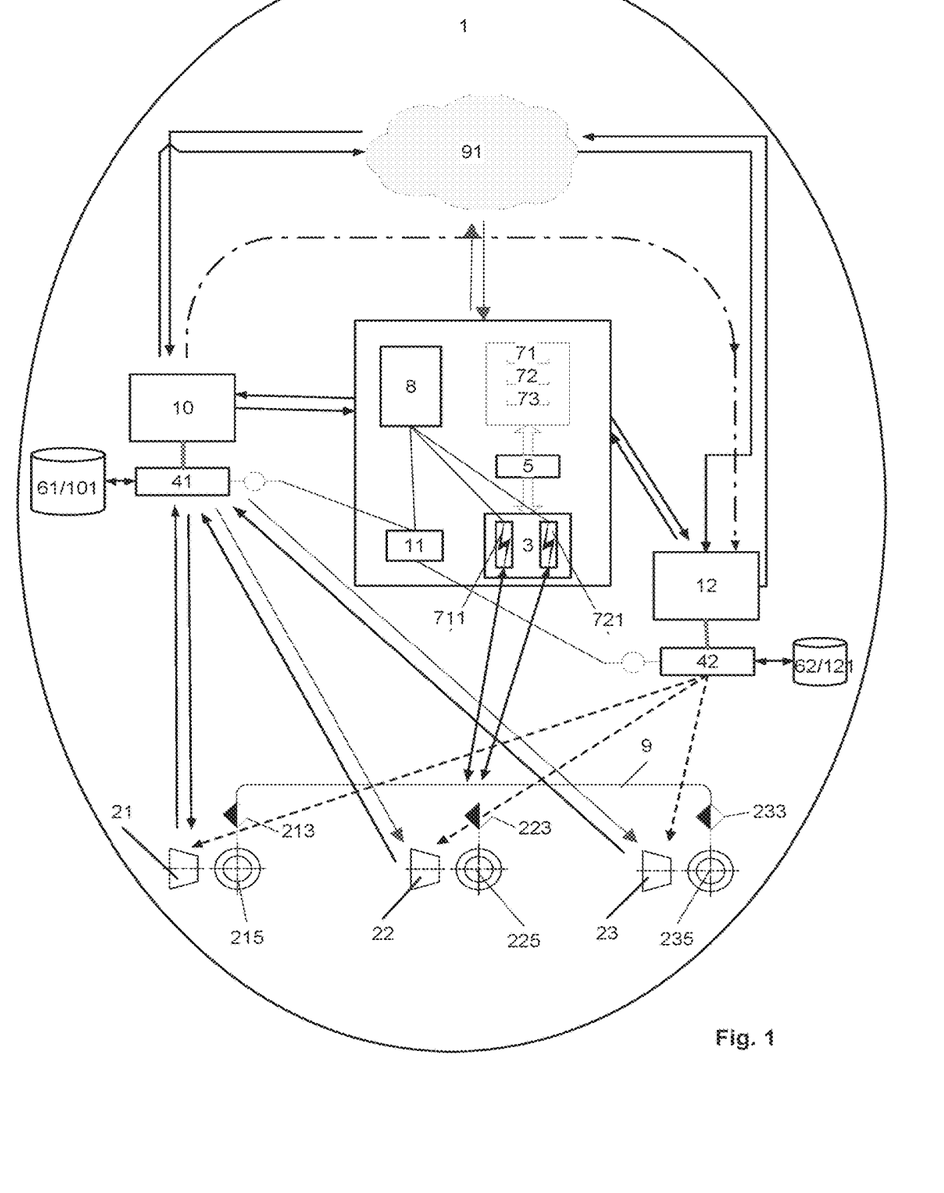
FIG. 1 shows a block diagram schematically illustrating an exemplary convertibly triggered system 1 with an event-triggered switching device 3 and layered trigger structures 71, 72, 73 for complementary switching of two coupled, autonomously operated insurance systems by providing a self-sufficient risk protection of a variable number of risk exposure components 21, 22, 23 by means of two automated resource pooling systems 101, 121.
Figure 2:
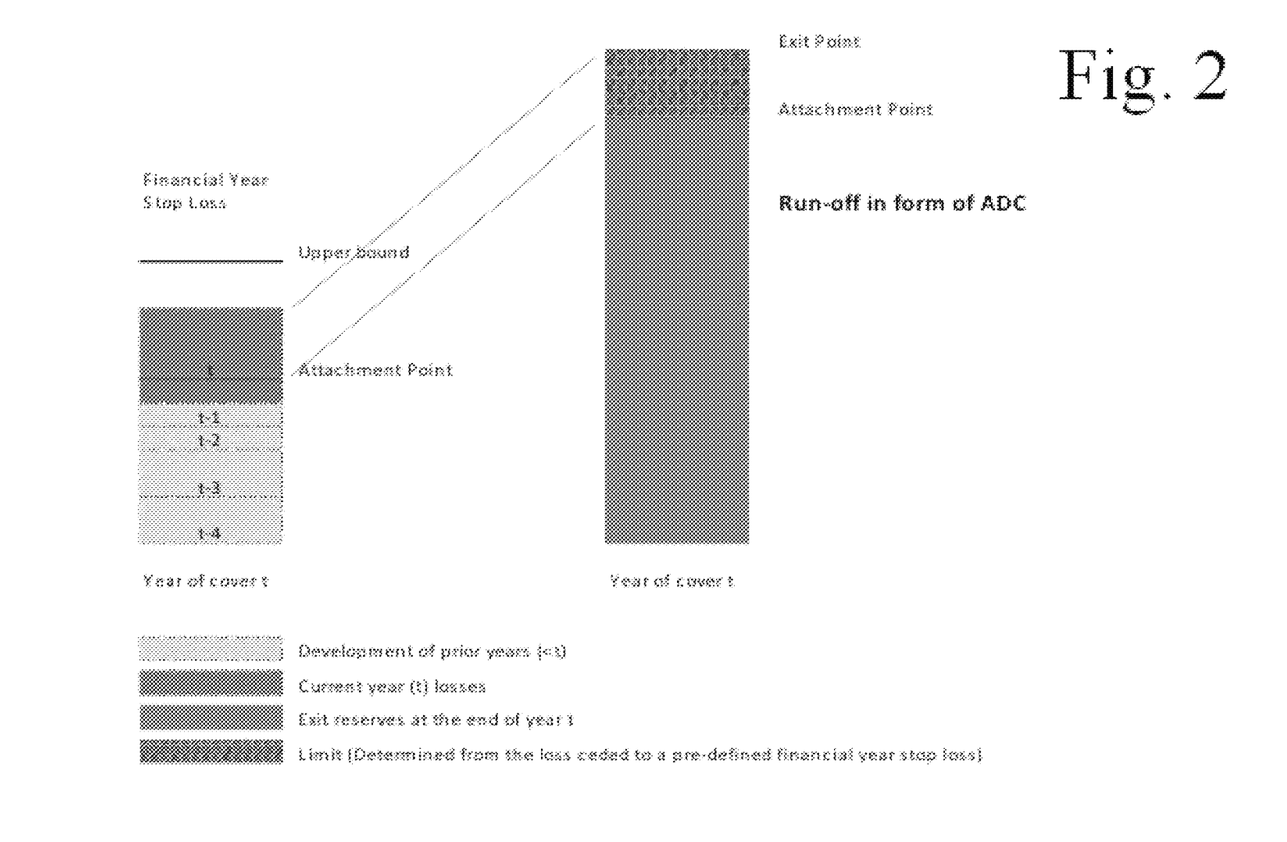
FIG. 2 shows a block diagram schematically illustrating the covering accumulations such as an Aggregate Stop/Adverse Development Cover on Year End Reserves as predefined time period. The result of the financial year stop loss determines the reinsurance limit available during run off in the form of an in-the-money adverse development cover.
Figure 3:
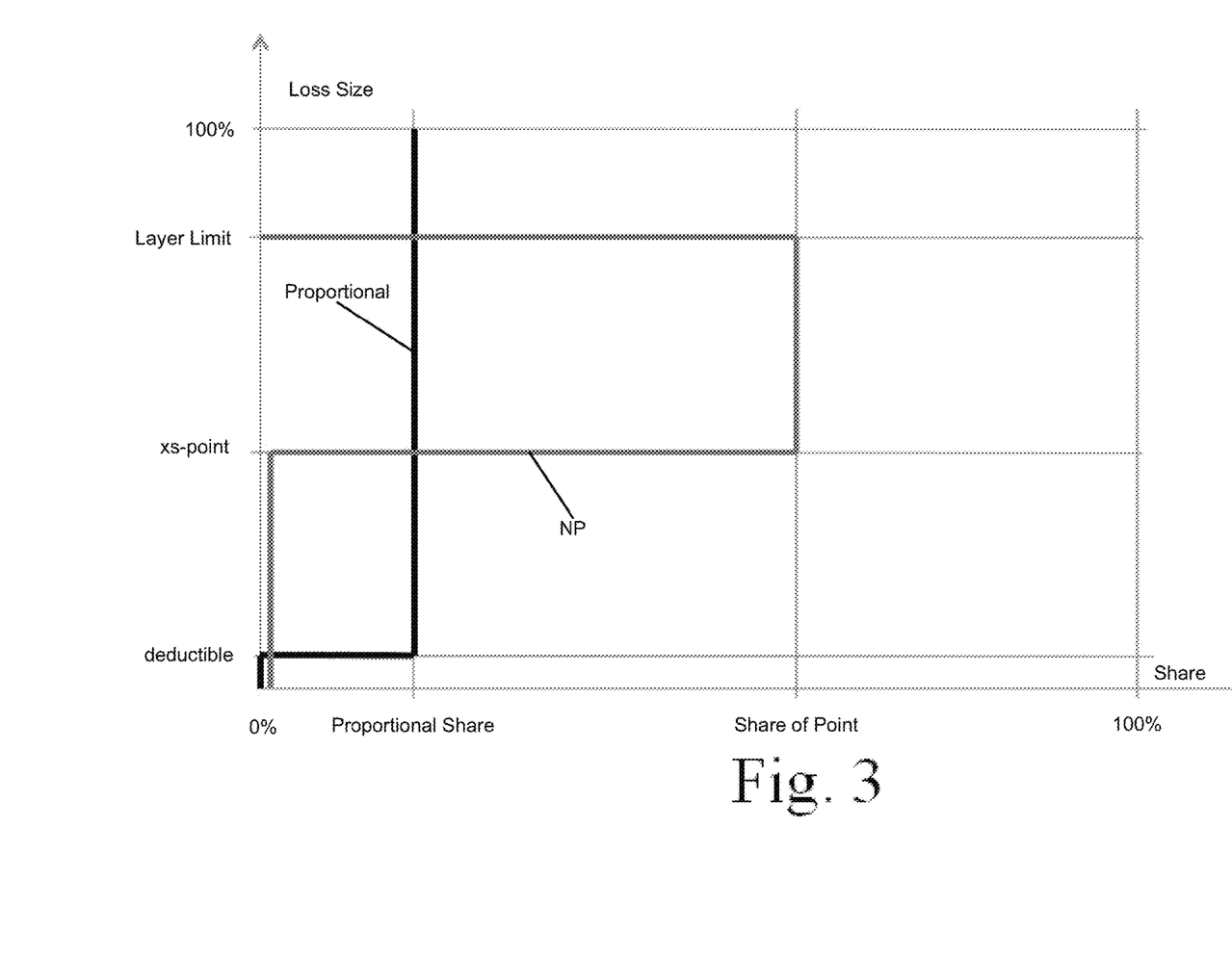
FIG. 3 shows a block diagram schematically illustrating the coupling structure of prior art systems using either a proportional or non-proportional switching structure.

FIG. 1 schematically illustrates an architecture for a possible implementation of an embodiment of the convertibly triggered system 1 with an event-triggered switching device 3 and layered trigger structures 71, 72, 73 for complementary switching of two coupled, autonomously operated insurance systems by providing self-sufficient risk protection of a variable number of risk exposure components 21, 22, 23 by means of two automated resource pooling systems 101, 121 that are associated with the insurance systems. The automated resource pooling systems 101, 121 comprise the first and second payment data store 61, 62 for their operation allowing a secure payment parameter storage. In FIG. 1, reference numeral 1 refers to the convertibly triggered system for providing optimized risk protection related to risk exposure components 21, 22, 23 . . . with the associated coupled resource pooling systems 101, 121. The resource pooling systems 101, 121, which are coupled, steered and/or operated by means of the control device 11, provide dynamic self-sufficient risk protection and a corresponding risk protection structure for the variable number of risk exposure components 21, 22, 23; i.e., units exposed to defined risk events, wherein the occurrence of such risk events is measurable and triggerable by means of appropriate measuring devices and/or trigger modules triggering in the data flow pathway of output data; i.e., measuring parameters of the measuring devices 215, 225, 235. The convertibly triggered system 1 includes at least one processor and associated memory modules. The convertibly triggered system 1 can also include one or more display units and operating elements, such as a keyboard and/or graphic pointing devices, such as a computer mouse. The resource pooling systems 101 and 121 are technical devices comprising electronic means that can be used by service providers in the field of risk transfer or insurance technology for the purpose of risk transfer as it relates to the occurrence of measurable risk events 501. The invention seeks to capture, handle and automate, by complex technical means, related operations of the automated insurance systems 10, 12, in particular in an effort to optimize the interaction of coupled systems 10, 12, and to reduce the operational requirements. Another aspect that is addressed is finding ways to synchronize and adjust such operations related to coupling or switching of resource pooling systems 101, 121, which are directed at proved risk protection of risk exposed units based on technical means. In contrast to the standard practice, the resource pooling systems 101, 121 also achieve reproducible, dynamically adjustable operations with the desired technical, repeating accuracy, because it is completely based on technical means, a process flow and process control/operation.

The control device 11 and/or the resource pooling systems 10 and 12 comprise an aggregation module 5 for processing risk-related component data 211, 221, 231 and for providing the likelihood 212, 222, 232 of said risk exposure for one or a plurality of the pooled risk exposure components 21, 22, 23, etc. based on the risk-related component data 211, 221, 231. The resource pooling systems 101 and 121 as well as the control device 11 can be implemented as a technical platform, which is developed and implemented to provide risk transfer through a plurality of (but at least one) payment transfer modules 41 and 42. The risk exposure components 21, 22, 23, etc. are connected to the resource pooling system 101 by means of the plurality of payment transfer modules 41 that are configured to receive and store payments 214, 224, 234 from the risk exposure components 21, 22, 23 for the pooling of their risks in a payment data store 61. The payments can be stored by transferring and storing component-specific payment parameters. The payment amount can be determined dynamically by means of the resource pooling system 101 based on total risk of the overall pooled risk exposure components 21, 22, 23. For the pooling of the resources, the system 1 can comprise a monitoring module 8 that requests a periodic payment transfer from the risk exposure components 21, 22, 23, etc. to the resource pooling system 101 by means of the payment transfer module 41, wherein the risk protection for the risk exposure components 21, 22, 23 is interrupted by the monitoring module 8, when the periodic transfer is no longer detectable via the monitoring module 8. In one alternative embodiment, the request for periodic payment transfers is automatically interrupted or waived by the monitoring module 8, when the occurrence of risk event indicators is triggered in the data flow pathway of a risk exposure component 21, 22, 23. Analogously, the first resource pooling system 101 is connected to the second resource pooling system 121 of the second insurance system 12 by means of a second payment transfer module 42 that is configured for receiving and storing payments from the resource pooling system 101 of the first insurance system for the transfer of risks associated with the pooled risk and risk exposures 50, respectively, of the risk exposure components 21, 22, 23 from the first insurance system 10 to the second insurance system 12. The coupling and switching of the two complementary, autonomously operated resource pooling systems 10, 12 is achieved by the event-triggered switching device 3 for generating and transmitting appropriate steering signals to the first and second resource pooling systems 101, 121.

As indicated in FIG. 1, the convertibly triggered system 1 includes a data storing module for capturing the risk-related component data and multiple functional modules; e.g., namely the payment transfer modules 41 and 42, the switching device 3 with a core engine with the triggers 711, 721, the aggregation module 5 or the operating module 75. The functional modules can be implemented at least partly as programmed software modules stored on a computer readable medium, connected in a fixed or removable manner to the processor(s) of the convertibly triggered system 1 or to associated automated systems 10,12. One skilled in the art understands, however, that the functional modules can also be implemented fully by means of hardware components, units and/or appropriately implemented modules. As illustrated in FIG. 1, the convertibly triggered system 1 and its components, in particular the first and second resource pooling systems 101, 121, the control device 11, the trigger modules 31,32, the measuring devices 215, 225, 235 with the interfaces 213, 223, 232, the aggregation module 5, and the payment transfer modules 41, 42, can be connected via a network 91, such as a telecommunications network or any other data transmission network. The network 91 can include a hard-wired or wireless network; e.g., the Internet, a GSM network (Global System for Mobile Communication), a UMTS network (Universal Mobile Telecommunications System) and/or a WLAN (Wireless Local Region Network), and/or dedicated point-to-point communication lines. In any case, the technical electronic money-related setup for the present system comprises adequate technical, organizational and procedural safeguards to prevent, contain and detect threats to the security of the structure, particularly counterfeiting threats. The resource pooling systems 101, 121 furthermore comprise all of the necessary technical means for electronic money transfer and link-up association; e.g., as initiated by one or more associated payment transfer modules 41, 42 via an electronic network. The monetary parameters can be based on any possible electronic and transfer means, such as e-currency, e-money, electronic cash, electronic currency, digital money, digital cash, digital currency, or cyber currency, etc., which can only be exchanged electronically. The first and second payment data stores 61, 62 provide the means for associating and storing monetary parameters associated with a single one of the pooled risk exposure components 21, 22, 23. The present invention can involve the use of the aforementioned networks, such as computer networks or telecommunication networks, and/or the internet and digital stored value systems. Electronic funds transfer (EFT), direct deposit, digital gold currency and virtual currency are further examples of electronic money modalities. Also, transfers can involve technologies such as financial cryptography and technologies for enabling such transfers. For the transaction of the monetary parameters, it is preferable to use hard electronic currency, without the technical possibilities for disputing or reversing charges. The resource pooling systems 101, 121 for example support non-reversible transactions. The advantage of this arrangement is that the operating costs of the electronic currency system are greatly reduced by not having to resolve payment disputes. However, this way, it is also possible for electronic currency transactions to clear instantly, making the funds available immediately to the systems 10, 12. This means that using hard electronic currency is rather akin to a cash transaction. However, it is also conceivable to use soft electronic currency, such as currency that allows for the reversal of payments, for example having a "clearing time" of 72 hours, or the like. The electronic monetary parameter exchange method applies to all connected systems and modules related to the resource pooling systems 101, 121 of the present invention, such as the first and second payment transfer modules 41, 42. The monetary parameter transfer to the first and second resource pooling system 101, 121 can be initiated by a payment transfer module 41 rsp. 42 or upon request by the related resource pooling system 101 or 121.

The system 1 comprises an event-driven switching device 3 with a core engine comprising the risk event triggers, i.e., the first and second layer trigger module 711, 721, for triggering component-specific measuring parameters in the data flow pathway 213, 223, 233 of the assigned risk exposure components 21, 22, 23. The data flow pathway 213, 223, 233 can for example be monitored by the system by means of measuring devices 215, 225, 235 that are connected to a data flow pathway 9 via the interfaces 213, 223, 233; in particular, it can be monitored by the resource pooling systems 101 and/or 121 and/or the control device 11, thereby capturing component-related measuring parameters of the data flow pathway 213, 223, 233 at least periodically and/or within predefined time periods. According to one alternative embodiment, the data flow pathway 213, 223, 233 can for example also be dynamically monitored by the convertibly triggered system 1, such as by triggering component-measuring parameters of the data flow pathway 213, 223, 233 that are transmitted from associated measuring systems 215, 225, 235. By triggering the data flow pathway 213, 223, 233, which comprises dynamically recorded measuring parameters of the concerned risk exposure components 21, 22, 23, the system 1 is able to detect the occurrence of predefined risk events based on predefined trigger parameters. Furthermore, the system 1 can for example also dynamically monitor different stages during the progress of the impact of a risk event on the risk exposure component 21, 22, 23 in order to provide appropriately adapted and gradated risk protection for a specific risk exposure component 21, 22, 23. Such a risk protection structure is based on received and stored payments 214, 224, 234 from the related risk exposure component 21, 22, 23 and/or related to the total risk exposure 50 of the resource pooling system 101, based on the overall transferred risks of all pooled risk exposure components 21, 22, 23.

The risk exposure components 21, 22, 23 of the convertibly triggered insurance system 1 are connected to the first insurance system 10 of the convertibly triggered system 1 by transferring risk exposure 50 associated with the occurrence of defined risk events 501 from the risk exposure components 21, 22, 23 to the first insurance system 10 by means of equitable, mutually aligned first risk transfer parameters 502 and correlated aligned first payment transfer parameters 503. The mutual alignment can be achieved by electronically negotiating and mutually adapting the parameters 502/503 over the network 91 via appropriately implemented interface modules of the first insurance system 10 and on the other side of the risk exposure components 21, 22, 23 based on dedicated optimization algorithms and means. For the further risk transfer, analogously, the first insurance system 10 is connected to the second insurance system 12 of the convertibly triggered system 1 by at least partially further transferring risk exposure 50 associated with the occurrence of the defined risk events 501 from the first insurance system 10 to the second insurance system 12 through equitable, mutually aligned second risk transfer parameters 504 and correlated aligned second payment transfer parameters 505. Again, the mutual alignment can be achieved by electronically negotiating and mutually adapting the parameters 504/505 over the network 91 by means of appropriately implemented interface modules of the first insurance system 10 on the one hand and the second insurance system 12 on the other hand, based on dedicated optimization algorithms and means/modules.

If one of the defined risk event 501 occurs, loss parameters measuring the loss at the risk exposure components 21, 22, 23 are captured from the data flow pathway 9 of the measuring devices 215, 225, 235 and transmitted to the first insurance system 10, wherein the occurred loss is automatically covered by the first insurance system 10 based on the equitable, mutually aligned second risk transfer parameters 504.

The convertibly triggered system 1 comprises the first layer trigger structure 71 comprising an aggregation module 5 for capturing and automatically aggregating captured loss parameters 92 over all risk exposure components 21, 22, 23 and all occurrences of risk events 501 within a predefined time period 713 by incrementing an associated stored aggregated loss parameter 93. By triggering the aggregated loss parameter 93 exceeding a defined stop loss threshold value 712 via the first trigger module 711 of the first layer trigger structure 71, the occurred loss 92 exceeding the defined stop threshold value 712 is automatically covered by the second insurance system 10 based on the equitable, mutually aligned second risk transfer parameters 504. The defined stop loss threshold value 712 can be negotiated together with the mutual alignment parameters 504/505, e.g., electronically by mutually adapting the parameters 504/505 over the network 91 by means of said implemented interface modules of the first insurance system 10 on the one hand and the second insurance system 12 on the other hand, based on dedicated optimization algorithms and means/modules.

There are different boundary condition parameters, which should be considered by the systems 10/12, in order to automatically negotiate the defined stop loss threshold value 712. The first insurance system 10 uses the second insurance system 12 as part of its management structures for its portfolio of pooled risks. The main use of the second insurance system component 12 is to allow the first insurance system 10 to protect the solvency of the company against an accumulation of claims associated with unexpected triggering of exceeding the aggregated loss parameter 93 of the defined loss threshold value 712. This can also for example be induced by catastrophic cases, wherein the first insurance system cannot keep up operation after a large loss. Therefore, the second insurance system 12 can improve the stability of the first insurance system 10 by reducing the amount of net liability. In the present invention, the system uses a non-proportional risk-transfer structure by means of the defined loss threshold value 712, i.e., excess of loss risk transfer, since the activation of the second insurance system 12 is only triggered if the loss suffered by the insurer exceeds a certain amount, i.e., the retention threshold value 722. However, it is important to note that the inventive structure of the system can also be applied to proportional risk transfer structures, e.g. as result of the QS triggering an ADC.

The convertibly triggered system 1 further comprises an intermediate layer trigger structure 73 with an associated switching device 3. By triggering the aggregated loss parameter 93 exceeding said defined stop threshold value 712 by means of the first trigger module 711, the second layer trigger structure 72 of the convertibly triggered system 1 is automatically activated by means of the switching device 3 of the intermediate layer trigger structure 73.

Finally, a second layer trigger structure 72 comprises a second trigger module 721. If the second layer trigger structure 72 is activated via the switching device 3 by triggering loss parameters 92 measuring the loss at the risk exposure components 21, 22, 23 not to be transmitted to the convertibly triggered system 1 within the predefined time period and falling outside a retention threshold value 722 of the first insurance system 10, the occurred loss exceeding said retention threshold value 722 is automatically covered by the second insurance system 12 based on the equitable, mutually aligned second risk transfer parameters 504.

If the aggregated loss parameter 93 is triggered exceeding said defined stop threshold value 712 and activating the second layer trigger structure 72 of the convertibly triggered system 1 via the switching device 3, the first layer trigger structure 71 can automatically be set to an equal time period 714 subsequent to the predefined time period 713, wherein the operation of the first layer trigger structure 71 is extended to said subsequent time period 714 and wherein the value of the incremented associated aggregated loss parameter 93 is reset to 0. In said subsequent time period 714, the operation of the system 1 is set to the same defined stop threshold value 712 and same retention threshold value 722 as defined in the preceding defined time period 713.

Through the measures of the pooled risk, an risk transfer structure is provided by the first, intermediate, and second layer trigger structure 71, 72, 73 via the assembly module 5. For example, the risk transfer structure is given by means of the assembly module 5 by aggregating the loss parameter 93 and triggering based on the mutually negotiated first risk and payment parameters 502,503 and the second risk and payment parameters 504, 505.

The stop threshold value 712, the time period 713, and the retention threshold value 722 can be self-adapted or negotiated by the system 1, thereby optimizing the operation resulting from the risk transfer structure. However, the optimization can also be performed by dedicated external means. The system 1 and/or the dedicated external means can for example perform the optimization until a local or global maximum or minimum, respectively, is achieved, or until a predefined target value is achieved. Finally, the optimization can be based on different sets of optimization criteria or a specific selection of a certain set of optimization criteria. As a condition for optimization, it is clear that the risk transfer structure 71, 72, 73 should be related to the assumed or predicted risk, and preferably, if the risk assessment is correct, to the occurrence of the corresponding risk events within the defined time frame. In one alternative embodiment, the trade-off between frequency and severity can be considered, as a boundary condition, to achieve a preferred or optimized risk transfer structure, wherein the severity is the conditional expected loss. An optimization criterion can for example be to vary the parameters 712, 713, 722, in order to minimize the variance of the retained loss of the first insurance system 10, for example, under the assumption that the payment transferred from the first insurance system 10 to the second insurance system 12 is generated by an expected value principle. However, the optimization criteria can for example be extended in any direction including further optimization criteria or payment transfer principles, such as considering mean-variance premium principles including the standard deviation principle and the variance principle. Other optimization criteria can for example be achieved by applying risk measures such as the value at risk (VaR) or the conditional value at risk (CVaR) for quantifying the risk, e.g., in particular by minimizing the VaR or CVaR of the total risk exposure of the first insurance system 10 under the assumption of the expected value premium principle. Furthermore, constraints can for example be incorporated reflecting either the profitability guarantee or the maximum amount of transferable payments from the first insurance system 10 to the second insurance system 12. However, further optimization criteria and constraints can be applied in any form needed to approach a specific risk transfer problem by means of the system 1.

Using the control device 11, a payment parameter 731, 732, 733 is assigned to a triggering of the stop loss threshold value 712 for the transfer of a specific part of the pooled risks of the first resource pooling system 10 based on the risk transfer structure 71, 72, 73 to the second resource pooling system 12. The payment parameters 731, 732, 733 can be accumulated to a total payment sum, wherein the control device 11 comprises a capturing device 111 for capturing payment transfer parameters 731, 732, 733 from the first payment transfer module 41 to the second payment transfer module 42. Upon triggering a transfer of the total payment sum at the second payment transfer module 42, the risk exposure of the first insurance system 10 associated with the variable risk transfer segments 721, 722, 723 has been transferred to the second insurance system 12. In one alternative embodiment, the control device 11 can further comprise capturing means 11 for capturing the transfer of payment from the first insurance system 10 to the second payment transfer module 42, wherein the second insurance system 12 can only be activated as a result of triggering an appropriate payment, and wherein the risk exposure of the first insurance system 10 associated with the assigned variable risk transfer segment 721, 722, 723 is transferred to the second insurance system 12 upon triggering the appropriate payment.

Furthermore, the switching device 3 comprises event-driven triggers 31, 32 for triggering measuring parameters in a data flow pathway 213, 223, 233 of measuring devices 215, 225, 235 associated with the risk exposure components 21, 22, 23 when a risk event occurs. The data flow pathways 213, 223, 233 can be connected to an overall data flow pathway 9 and/or to the network 91, as described above. The measuring devices 215, 225, 235 comprise the interfaces 213, 223, 233 for allowing data access to measuring devices 215, 225, 235. If an occurrence of a risk event is triggered in the data flow pathway 9, the corresponding activation signal is generated by the control device 11 based on the measured actual loss, wherein the control device 11 triggers the complementary activation of the first and second resource pooling systems 10, 12 via the generated activation signal by transferring the activation to the first and/or second resource pooling system 101, 121 in order to provide risk protection to the risk exposure components 21, 22, 23. In this way, the present invention provides the utmost flexibility and an optimal technical solution for coupled and complementary switched insurance systems with associated resource pooling systems 10, 12. The invention allows for applying proportional and non-proportional risk transfer structures. Furthermore, as described above, the inventive system 1 is based on the described optimization process, wherein the optimization criteria can also be implemented for a consideration of boundary criteria, as provided by the requirements of the risk-exposed components 21, 22, 23 and/or the first and/or second resource pooling systems. In addition, it is a fundamental aspect of the system that the transferred risk shares can be made to depend only on the loss size that is associated with the impact of a risk event with regard to a risk exposure component 21, 22, 23. The operational mode, in which the risk shares depend on the loss size, can be optimized by the appropriate means of the system 1. The need for optimized risk transfer systems intensifies with increasing loss size; e.g., the optimization criteria can be compared to the overall risk that is transferred to the first resource pooling system 10, i.e., the risk portfolio of the first resource pooling system 10, before and after the risk transfer.

In addition to the adaptation of the triggers 31, 32, 33, the amount of requested payments from the risk exposure components 21, 22, 23 can be adjusted accordingly by the system 1 and/or the resource pooling system 101. Therefore, the receipt and preconditioned storage 61 of payments 214, 224, 234 from risk exposure components 21, 22, 23 for the pooling of their risks can be determined dynamically, based on total risk 50 and/or the likelihood of the risk exposure of the pooled risk exposure components 21, 22, 23 to improve the operational and functional security of the system 1 even further. The number of pooled risk exposure components 21, 22, 23, can be dynamically adapted by means of the system 1 and/or the resource pooling system 10 to a range where non-covariant occurring risks that are covered by the resource pooling system 1 affect only a relatively small proportion of the total pooled risk exposure components 21, 22, 23 at any given time. In another variant, the pooled risk transfers from first resource pooling systems 10 can also be dynamically adaptable by means of the second resource pooling system 12 to a range where non-covariant occurring risks covered by the second resource pooling system 12 affect only a relatively small proportion of the total pooled risk transfers from first resource pooling systems 10 at any given time. The triggering parameters of the covered risk events can be contained and stored in a predefined searchable table, such as an appropriately structured hash table, of predefined risk events, respectively risk event parameters. The corresponding losses occur as a result of a risk event at risk exposure components 21, 22, 23, . . . with regard to one of the searchable risk events; i.e., the possible need of risk exposure components 21, 22, 23, . . . to be covered by the pooled resources of the resource pooling systems 10,12 is linked to the risk of the occurrence of a risk event that requires resolving the loss in order to avoid operational interruption, or the like.

If an occurrence of a risk event is triggered on the data flow pathway 213, 223, 233 of a risk exposure component 21, 22, 23, i.e., if triggering of an occurrence of a risk event goes into effect in the data flow pathway 213, 223, 233, a corresponding trigger-flag, for instance, can be activated by means of the resource pooling system 10, and a parametric or otherwise predefined transfer of payments, e.g., the measured excess of loss, can be assigned to this corresponding trigger-flag. An excess of loss associated with the occurrence of risk events can for example be covered by the resource pooling system 101, based on the respective trigger-flag and based on the received and stored payment parameters 214, 224, 234 from risk exposure components 21, 22, 23 via the parametric or otherwise predefined transfer from the resource pooling system 10 to the risk exposure component 21, 22, 23, etc. The payment transfer modules 41, 42 can, as an input device, comprise one or more data processing units, displays and other operating elements, such as a keyboard and/or a computer mouse or another kind of pointing device. As previously mentioned, the receiving operation of the payments with regard to the risk exposure components 21, 22, 23 is monitored based on the stored component-specific payment parameters in the payment data store 61. The different components of the system 1, such as the resource pooling systems 101, 121, the control device 11, the payment transfer modules 41, 42, the switching device 3 and the assembly module 5 can be connected via a network 91 for signal transmission. The network 91 can for example comprise a telecommunications network, such as a hardwired or wireless network, e.g., the Internet, a GSM network (Global System for Mobile Communications), a UMTS network (Universal Mobile Telecommunications System) and/or a WLAN (Wireless Local Area Network), a Public Switched Telephone Network (PSTN) and/or dedicated point-to-point communication lines. The payment transfer modules 41, 42 and/or core engine 3 and the assembly module 5 can also comprise a plurality of interfaces for connecting to the telecommunications network while adhering to the transmission standard or protocol. In one alternative embodiment, the payment transfer module 41, 42 can also be implemented as an external device relative to the system 1, which provides the risk transfer service via the network for signal transmission, e.g., by a secured data transmission line.

Finally, in a further specified alternative embodiment, an independent verification risk event trigger of the system 1 can be activated in the event the occurrence of indicators for one of the predefined risk events or level of excess of loss is triggered in the data flow pathway 213, 223, 233 of a risk exposure component 21, 22, 23, etc. by means of the risk event trigger 31, 32, and wherein the independent verification risk event trigger, additionally, is triggered with regard to the occurrence indicators for one of the predefined risk events in an alternative data flow pathway 215, 225, 235 with independent measuring parameters from the primary data flow pathway 213, 223, 233 in order to verify the occurrence of the risk event at the risk exposure component 21, 22, 23, etc. As an alternative, the parametric or otherwise predefined transfer of payments is only assigned to the corresponding trigger-flag when the occurrence of the risk event at the risk exposure component 21, 22, 23, etc. has been verified by the independent verification risk event trigger.

In summary, the operational parameters of the convertibly triggered system 1 can be tuned by providing various retrospectively and/or prospectively layered risk transfer structures for covering and transferring first insurance systems' risk exposure with regard to or regardless of the intensity of the actually-occurring risk events. The mutual tuning of the operational parameters of the convertibly triggered system layers allows for tuning of the operational parameters of various retrospective operation layers of the convertible system, such as stop loss risk transfer or finite risk transfer, or such as adverse development cover (ADC) of risk transfers or loss portfolio transfer (LPT) cover of risk transfers and/or together with the operational parameters of prospective operation layers of the convertible system, such as quota share risk transfer, founded cover risk transfer, spread loss risk transfer, or in general blended cover risk transfer. In particular, for the operation of an automated risk transfer system, it is important that the system can be operated self-sufficiently, i.e., with economic finality concerning the automatically pooled and managed resources. Therefore, the convertibly triggered system makes it possible to combine risk transfer of stop loss cover with risk transfer of adverse development cover and/or loss portfolio transfer cover, providing a self-sufficient operatable, automatable risk transfer system, which cannot be found in the prior art systems. In particular, the prior art systems do not allow for mutually tuning the operational parameters of risk transfers of techniques such as stop loss transfers with techniques such as adverse development cover and/or loss portfolio transfer cover, providing an overall optimization of the parameters together with the technical requirement of self-sufficiency of the system. The convertibly triggered system 1 further provides the technical requirements for a multi-period optimization of the operational parameters of a layered risk-transfer system. Thus, using the result of the predefined time period, e.g., a financial year, the applied stop loss risk transfer can determine the second insurance system limit available during run off in the form of an in-the-money adverse development cover. The invention provides supremely optimized layer-based coupling also optimizing the classically prevalent optimization problem of managing the two coupled risk transfer systems, seeking better and more effective operation and strategies based on an appropriate risk transfer structure. The convertibly triggered system 1 therefore needs smaller pooled resources, in contrast to traditional coupled resource pooling systems, to allow for a safe operation of the system. In addition, the operational aspects of the system are transparent to operators as well as covered risk units, since payment is transferred in response to individually adaptable risk transfer structures and related to certain definable triggers in the context of the information pathways. The inventive system provides a new modality for optimizing the underlying risk transfer structure in the service of risk transfer and sharing of two coupled insurance systems by using several layers of different risk transfer strategies. Thereby, the invention has strategic and operational advantage that, for the risk-exposed components as well as for the first insurance system, operationally allow for an all-inclusive balance sheet and capital protection (with some exclusions). The present convertible invention is additionally capable, owing to its technical structure, of protecting against unknown accumulation, including contribution from prior years. This is normally not possible in the known prior art system, since their structure is typically solely directed to single risks. However, if the prior art system allow capturing different risks, the prior art risk transfer structures are only able to capture single risk categories and do not allow for an open self-sufficient risk transfer system without the requirement of risk categorization, as the present invention does. The operation of the present invention also compares favorably to an Adverse Development Cover in terms of budget in view of contingent nature. The invention allows for operational optimization, which makes it very efficient under all available economic capital models underlying prior art systems. Furthermore, the present system allows automatic renewal of the operation and optimization of the appropriate operational parameters for optimized coverage within the subsequent defined time period, e.g., annually. Lastly, the system of the present invention provides the technical structure to be applicable and/or operatable with respect to all forms of accumulation risks, i.e., inter alia, classic clash risk transfers, serial aggregation risk transfers, business disaster risk transfers, systemic failure risk transfers, etc. Further, since the system is able to commute the adverse development cover (ADC), i.e. the adverse development risk transfer, after a predefined period, e.g. 5-10 years, the invention has the advantage of limiting the tail exposure but allowing enough time for the reserves to reach a more or less stable level in respect to the operation of the system. Further, it expedites the cash flows for the primary risk transfer system, i.e. the first automated insurance system, and reduces the administrative burden of all involved parties caused by extremely long payout patterns (i.e. small partial payments over a period of time of e.g. 40 years). It has to be mentioned that the conventional financial year stop loss risk transfer can be favorable from the risk exposure components perspective. However, from the operational perspective of an automated and coupled second risk transfer system, this has a couple of severe drawbacks, which drive the amount of pooled resources, i.e. the necessary premiums to be transferred, at the second coupled risk transfer system, e.g. a coupled, automated reinsurance system, to a level that is in most cases not anymore economically realizable for first or primary insurance systems. The main problem from a second coupled risk transfer system's perspective lies in the fact that the primary risk transfer system has an information advantage in regards of the expectation of the reserves development and that the primary risk transfer system can influence or even manipulate the reserve level in a way that would trigger a financial year stop loss treaty. Let's assume that the primary risk transfer system overstated the reserves by 10 in the financial year 2014 in a way that the stop loss treaty 2014 would be triggered and give a cover of 10. If in 2015 the primary risk transfer system releases the 10 in reserves again, the second risk transfer system would still need to pay under the financial year stop loss of 2014. With the Morph structure, this cheating element is addressed for the coupled systems and reduced to an extent that a financial year stop loss can be offered at an affordable price.

The invention claimed is:

1. An optimized and stable, automated system for sharing risks of occurring, measurable risk events of a variable number of defined risk exposure components with a mutually tuned trigger structure providing a dynamically morphing, self-sufficient risk protection structure; the system comprising:

the risk exposure components that are connected to a first automated resource pooling system of an automated first insurance system of the system and that transfer risk exposure associated with an occurrence of defined risk events from the risk exposure components to the first insurance system based on equitable; mutually aligned first risk transfer parameters and correlated aligned first payment transfer parameters;

the first insurance system that is connected to a second automated resource pooling system of an automated second insurance system of the system and that transfers risk exposure associated with the occurrence of the defined risk events from the first insurance system to the second insurance system based on equitable, mutually aligned second risk transfer parameters and correlated aligned second payment transfer parameters, wherein:

when one of the defined risk events occurs, loss parameters measuring a loss at the risk exposure components are captured and transmitted to the first insurance system, and an occurred loss is automatically covered by the first automated resource pooling system of the first insurance system based on the equitable, mutually aligned second risk transfer parameters;

a first layer trigger structure including circuitry configured to:

capture and automatically aggregate captured loss parameters overall risk exposure components and all occurrences of risk events within a predefined time period by incrementing an associated stored aggregated loss parameter, trigger the aggregated loss parameter exceeding a defined stop loss threshold value, whereby the occurred loss exceeding the defined stop threshold value is automatically covered by the second automated resource pooling system of the second insurance system based on the equitable, mutually aligned second risk transfer parameters, and a second layer trigger structure of the system is automatically activated by a switching device of an intermediate layer trigger structure; and the second layer trigger structure, wherein when the second layer trigger structure is activated via the switching device by triggering loss parameters measuring the loss at the risk exposure components not to be transmitted to the system within the predefined time period and falling outside a retention threshold value of the first insurance system, the occurred loss exceeding said retention threshold value is automatically covered by the second insurance system based on the equitable, mutually aligned second risk transfer parameters, and wherein for the coupling and switching of the two complementary, autonomously operated resource pooling systems, the event-triggered switching device generates and transmits appropriate steering signals to the first and second automated resource pooling systems.

2. The system according to claim 1, wherein
by triggering the aggregated loss parameter exceeding said defined stop threshold value and by activating the second layer trigger structure of the system via the switching device, the first layer trigger structure is automatically set to an equal time period subsequent to the predefined time period, and
an operation of the first layer trigger structure is extended to said subsequent time period and a value of the incremented associated aggregated loss parameter is reset to 0.

3. The system according to claim 2, wherein, in said subsequent time period, the operation of the system is set to the same defined stop threshold value and same retention threshold value as defined in a preceding defined time period.

4. The system according to claim 1, wherein the risk exposure components are connected to the first insurance system of the system by the circuitry, the circuitry being configured to receive and store first payment parameters from the risk exposure components for the transfer of risks associated with the risk exposure components from the risk exposure components to the first insurance system.

5. The system according to claim 1, wherein the first insurance system is connected to the second insurance system of the system by the circuitry, the circuitry being configured to receive and store second payment parameters from the first insurance system for the transfer of risks associated with pooled risk exposures of the risk exposure components from the first insurance system to the second insurance system.

6. The system according to claim 1, wherein the switching device includes a control device to capture a payment transfer from the first insurance system to the circuitry, the second layer trigger structure of the system being activated by triggering a payment transfer matching a predefined activation control parameter.

7. The system according to claim 1, wherein
a loss associated with the risk event and allocated to a pooled risk exposure component is distinctly covered by automated resource pooling systems of the first insurance system via a transfer of payments from the first resource pooling system to said risk exposure component, and
a second payment transfer from an automated second resource pooling system of the second insurance system to the first resource pooling system is triggered via the generated activation signal based on the measured actual loss of the risk exposure component of a definable risk transfer function provided by the system.

8. The system according to claim 7, wherein
the loss corresponding to the risk event that is transferred to the second resource pooling system is directly covered by the second resource pooling system through the transfer of resources from the second resource pooling system to the concerned risk exposure components via the circuitry.

9. The system according to claim 1, wherein the circuitry is configured to access and mutually adapt the risk transfer function prior to the transfer of the payment parameters from the first insurance system to the second insurance system.

10. The system according to Maim 1, wherein
the circuitry is configured to process risk-related component data and provide the likelihood of the risk exposure for one or a plurality of the pooled risk exposure components based on risk-related component data, and
receipt and preconditioned storage of payments from risk exposure components for the pooling of their risks are dynamically determined based on total risk and/or the likelihood of the risk exposure of the pooled risk exposure components.

11. The system according to claim 1, wherein
the circuitry is configured to process risk-related component data and provide the likelihood of said risk exposure for one or a plurality of the pooled risk exposure components based on risk-related component data, and
receipt and preconditioned storage of payments from first resource pooling system to the second resource pooling system for the transfer of its risk are dynamically determined based on total risk and/or the likelihood of the risk exposure of the pooled risk exposure components.

12. The system according to claim 1, wherein a number of pooled risk exposure components is dynamically adapted via the first insurance system to a range where non-covariant occurring risks covered by the first insurance system affect only a relatively small proportion of the total pooled risk exposure components at any given time.

13. The system according to claim 1, wherein the pooled risk transfer from the first resource pooling system is dynamically adapted via the second insurance system to a range where non-covariant occurring risks covered by the second insurance system affect only a relatively small proportion of the total pooled risk transfer from the first insurance system at any given time.

14. The system according to claim 1, wherein the circuitry is dynamically adapted based on time-correlated incidence data for one or a plurality of risk events.

15. The system according to claim 1, wherein
upon each triggering of an occurrence of measuring parameters indicating a risk event, a total parametric payment is allocated with the triggering, and
the total allocated payment is transferable when the occurrence has been triggered.

16. The system according to claim 1, wherein the activation of the first and/or second resource pooling system is based on the adaptable risk transfer function directly providing threshold values for a complementary switching and activation of the first and/or second insurance system, respectively.

17. An optimized method for a stable, automated system for sharing risks of occurring and measurable risk events of a variable number of defined risk exposure components with a mutually tuned trigger structure, the method comprising:
capturing and transmitting loss parameters measuring a loss at risk exposure components to a first insurance system, in a case of an occurrence of one of defined risk events;
automatically covering an occurred loss by a first automated resource pooling system of the first insurance system based on equitable, mutually aligned second risk transfer parameters;
capturing and automatically aggregating captured loss parameters overall risk exposure components and all occurrences of risk events within a predefined time period by incrementing an associated stored aggregated loss parameter; and triggering the aggregated loss parameter exceeding a defined stop loss threshold value, whereby the occurred loss exceeding the defined stop threshold value is automatically covered by a second automated resource pooling system of an automated second insurance system based on the equitable, mutually aligned second risk transfer parameters, and a second layer trigger structure of the system is automatically activated by a switching device of an intermediate layer trigger structure, wherein when the second layer trigger structure is activated via the switching device by triggering loss parameters measuring the loss at the risk exposure components not to be transmitted to the system within the predefined time period and falling outside a retention threshold value of the first insurance system, the occurred loss exceeding said retention threshold value is automatically covered by the second automated resource pooling system of the automated second insurance system based on the equitable, mutually aligned second risk transfer parameters;

risk exposure components are connected to the first automated resource pooling system of the automated first insurance system of the system and transfer risk exposure associated with the occurrence of defined risk events from the risk exposure components to the first insurance system based on equitable, mutually aligned first risk transfer parameters and correlated aligned first payment transfer parameters; and the first insurance system is connected to the second automated resource pooling system of the automated second insurance system of the system and transfers risk exposure associated with the occurrence of the defined risk events from the first insurance system to the second insurance system based on the equitable, mutually aligned second risk transfer parameters and correlated aligned second payment transfer parameters.

18. A non-transitory computer readable medium having a computer program recorded thereon, the computer program configured to perform a method for a stable, automated system for sharing risks of occurring and measurable risk events of a variable number of defined risk exposure components with a mutually tuned trigger structure when executed on a computer, the method comprising:

capturing and transmitting loss parameters measuring a loss at risk exposure components to a first insurance system, in a case of an occurrence of one of defined risk events;

automatically coveting an occurred loss by a first automated resource pooling system of the first insurance system based on equitable, mutually aligned second risk transfer parameters;

capturing and automatically aggregating captured loss parameters overall risk exposure components and all occurrences of risk events within a predefined time period by incrementing an associated stored aggregated loss parameter; and triggering the aggregated loss parameter exceeding a defined stop loss threshold value, whereby the occurred loss exceeding the defined stop threshold value is automatically covered by a second automated resource pooling system of an automated second insurance system based on the equitable, mutually aligned second risk transfer parameters, and a second layer trigger structure of a system is automatically activated by a switching device of an intermediate layer trigger structure, wherein when the second layer trigger structure is activated via the switching device by triggering loss parameters measuring the loss at the risk exposure components not to be transmitted to the system within the predefined time period and falling outside a retention threshold value of the first insurance system, the occurred loss exceeding said retention threshold value is automatically covered by the second automated resource pooling system of the automated second insurance system based on the equitable, mutually aligned second risk transfer parameters;

risk exposure components are connected to the first automated resource pooling system of the automated first insurance system of the system d transfer risk exposure associated with the occurrence of defined risk events from the risk exposure components to the first insurance system based on equitable, mutually aligned first risk transfer parameters and correlated aligned first payment transfer parameters; and the first insurance system is connected to the second automated resource pooling system of the automated second insurance system of the system and transfers risk exposure associated with the occurrence of the defined risk events from the first insurance system to the second insurance system based on the equitable, mutually aligned second risk transfer parameters and correlated aligned second payment transfer parameters.

\* \* \* \* \*